United States Patent
Han

(10) Patent No.: US 10,398,670 B2
(45) Date of Patent: *Sep. 3, 2019

(54) ORAL MICROBIOTA PROMOTION FOR ORAL AND/OR SINUS INFECTIONS

(71) Applicant: Knoze Jr. Corporation, Los Alamos, NM (US)

(72) Inventor: Shunsheng Han, Los Alamos, NM (US)

(73) Assignee: Knoze Jr. Corporation, Los Alamos, NM (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/706,323

(22) Filed: Sep. 15, 2017

(65) Prior Publication Data

US 2018/0303782 A1 Oct. 25, 2018

Related U.S. Application Data

(63) Continuation-in-part of application No. 15/495,188, filed on Apr. 24, 2017, now Pat. No. 9,795,579.

(51) Int. Cl.

| | | |
|---|---|---|
| *A61K 31/198* | (2006.01) | |
| *A61K 9/00* | (2006.01) | |
| *A61K 31/702* | (2006.01) | |
| *A61K 31/7016* | (2006.01) | |
| *A61K 31/719* | (2006.01) | |
| *A61K 31/733* | (2006.01) | |
| *A61K 35/644* | (2015.01) | |
| *A61K 36/736* | (2006.01) | |
| *A61K 36/54* | (2006.01) | |
| *A61K 36/898* | (2006.01) | |
| *A23L 33/135* | (2016.01) | |
| *B08B 3/10* | (2006.01) | |
| *A61K 36/185* | (2006.01) | |
| *A61P 31/00* | (2006.01) | |

(52) U.S. Cl.
CPC .......... *A61K 31/198* (2013.01); *A23L 33/135* (2016.08); *A61K 9/0053* (2013.01); *A61K 9/0056* (2013.01); *A61K 31/702* (2013.01); *A61K 31/7016* (2013.01); *A61K 31/719* (2013.01); *A61K 31/733* (2013.01); *A61K 35/644* (2013.01); *A61K 36/185* (2013.01); *A61K 36/54* (2013.01); *A61K 36/736* (2013.01); *A61K 36/898* (2013.01); *A61P 31/00* (2018.01); *B08B 3/10* (2013.01); *A23V 2002/00* (2013.01)

(58) Field of Classification Search
CPC .......................... A61K 9/0056; A23L 33/135; A23V 2002/00; B08B 3/10
See application file for complete search history.

(56) References Cited

U.S. PATENT DOCUMENTS

| | | | | | |
|---|---|---|---|---|---|
| 5,558,071 | A * | 9/1996 | Ward | ........................ | F02P 3/02 123/598 |
| 6,579,851 | B2 * | 6/2003 | Goeke | .................... | A61K 38/26 514/11.7 |
| 8,461,129 | B2 * | 6/2013 | Bolduc | ................... | A61L 15/28 127/49 |
| 2011/0028412 | A1 * | 2/2011 | Cappello | ............ | A61K 31/7004 514/25 |
| 2013/0041004 | A1 * | 2/2013 | Drager | ..................... | A61K 9/08 514/394 |
| 2013/0084243 | A1 * | 4/2013 | Goetsch | ............. | C07K 16/2863 424/1.49 |
| 2013/0096073 | A1 * | 4/2013 | Sidelman | ........... | A61K 38/1709 514/21.6 |
| 2016/0324766 | A1 | 11/2016 | Stettler et al. | | |

OTHER PUBLICATIONS

Tea Blog (https://beleaveteas.com/blog/three-delectable-teas-to-pair-with-your-thanksgiving-dinner-and-make-it-unforgettable/) available Jul. 11, 2015, pp. 1-5 (Year: 2015).*
Newman et al. "The effect of hot beverages, cold beverages, and chewing gum on oral temperature" Transfusion 2001, 41, 1241-1243 (Year: 2001).*
MyFood Data (https://tools.myfooddata.com/protein-calculator.php?foods=05220-05220-05220&serv=wt1-wt1-wt1&qty=1-1-1) accessed Nov. 30, 2018, pp. 1-2 (Year: 2018).*
Qian (https://archive.shine.cn/feature/health-and-environment/Soybean-milk-the-health-drink-for-all-seasons/shdaily.shtml) May 19, 2009, pp. 1-4 (Year: 2009).*

(Continued)

*Primary Examiner* — Andrew S Rosenthal
(74) *Attorney, Agent, or Firm* — James C. Kennedy, III, Esq, LLC; James C. Kennedy, III

(57) ABSTRACT

A method of promoting a desired oral microbiota to treat an oral and/or sinus infection condition in a subject in need of such treatment including providing a preformulated prebiotic edible composition including an amino acid containing ingredient comprising individual molecules of L-arginine; substantially removing a biofilm from surfaces within an oral cavity by heating the inside of the oral cavity to a temperature of about 100 deg F. to about 130 deg F.; wherein following removal of the biofilm, the composition is provided contained and at least partially dissolved within an oral cavity of the subject for a period of at least from about 30 seconds to about an hour on a daily basis of at least two consecutive days to promote an increased concentration of selected oral microbiota, the selected microbiota comprising *Veillonella* and *Streptococcus*, thereby treating the oral and/or sinus infection condition.

23 Claims, No Drawings

(56) References Cited

OTHER PUBLICATIONS

Wei (https://www.eater.com/2016/2/15/10995808/america-soymilk-fresh) Feb. 15, 2016, pp. 1-8 (Year: 2016).*

Hou et al. "Sugar Variation in Soybean Seed Assessed with a Rapid Extraction and Quantification Method" International Journal of Agronomy 2009, Article ID 484571, pp. 1-8 (Year: 2009).*

Kuiken et al. "Essential Amino Acid Composition of Soy Bean Meals Prepared From Twenty Strains of Soy Beans" J. Biol. Chem. 1949, 177:29-36 (Year: 1949).*

David P. Strachan, Hay fever, hygiene, and household size, Br. Med. j. 1989;299:1259-60, BMJ, United Kingdom.

H. Odkada, C. Kuhn, H. Feillet, and J.F.Bach,The 'hygiene hypothesis' for autoimmune and allergic diseases: an update, Clinical and Experimental Immunology, 2010:160:1-9, British Society for Immunology, United Kingdom, Wiley.

Samuel J. Arbes, Jr. et. al.,Can oral pathogens influence allergic disease?, May 2011,vol. 127, Issue 5, pp. 1119-1127, American Academy of Allergy, Asthma & Immunology, Elsevier Inc.,US.

Cliff Shunsheng Han, A specific hygiene hypothesis, Medical Hypotheses 93 (2016) 146-149, Elsevier Inc., US.

A. Tedeschi et. al., Clinical Exp. Allergy., 2003, 33:449, 454, Blackwell publishing, Oxford, England.

Caelos A. Cuello-Garcia et.al., Probiotics for the prevention of allergy: A systematic review and meta-analysis of randomized controlled trials, Oct. 2015 vol. 136, Issue 4, pp. 952-961,American Academy of Allergy, Asthma & Immunology, Elsevier Inc., US.

Hosana G. Rodrigues et. al., Fattyacids as modulators of neutrophil recruitment, function and survival, European Journal of Pharmacology 785(2016) 50-58, Elsevier Inc.,US.

Renan Oliveira Corrêa et. al., Regulation of immune cell function by short-chain fatty acids, Clinical & Translational Immunology (2016) 5, e73; doi:10.1038/cti.2016.17 & 2016 Australasian Society for Immunology Inc., Campinas, São Paulo, Brazil.

Ken Kikuchi et al., Comparison of Phenotypic Characteristics, DNA-DNA Hybridization Results, and Results with a Commercial Rapid Biochemical and Enzymatic Reaction System for Identification of Viridans Group Streptococci, Journal of Clinical Microbiology, May 1995, p. 1215-1222, American Society for Microbiology, US.

Alan L. Coykendall, Classification and Identification of the Viridans Streptococci, Clinical Microbiology Reviews, Jul. 1989, p. 315-328, American Society for Microbiology, US.

Jessica E. Koopman et al. ,Stability and Resilience of Oral Microcosms Toward Acidification and Candida Outgrowth by Arginine Supplementation, Microb Ecol (2015) 69:422-433, Springer Science+Business Media New York 2014.

J.A. Durant et al., Comparison of Batch Culture Growth and Fermentation of a Poultry *Veillonella* Isolate and Selected *Veillonella* Species Grown in a Defined Medium ,Anaerobe (1997) 3, 391-397,1997 Academic Press, US.

Jessica E. Koopman et al., Changes in the oral ecosystem induced by the use of 8% arginine toothpaste, Archives of Oral Biology 73 (2017) 79-87, 2016 Elsevier Ltd, US.

Ethan Kolderman et al., L-Arginine Destabilizes Oral Multi-Species Biofilm Communities Developed in Human Saliva, PLOS ONE | DOI:10.1371/journal.pone.0121835 May 6, 2015.

* cited by examiner

ORAL MICROBIOTA PROMOTION FOR ORAL AND/OR SINUS INFECTIONS

The disclosure generally relates to oral cavity microbiota promoting compositions including sweetened prebiotic foods and methods for making and using the same. More particularly, the disclosure relates to compositions and methods for making and using the same that may have the advantageous effect of modulating the oral microbiota which may thereby promote the naturally occurring health of the immune system including reducing respiratory allergic reactions as well as other oral and/or sinus infections.

BACKGROUND

In general, the prevalence of allergic diseases has dramatically increased in recent decades and currently affects more than sixty million people in the United States, reducing the quality of life. It is believed and has been found that the presence of certain oral bacteria species/strains may affect the aggressiveness of response of the immune system, for example with respect to allergies. More specifically, while not intending to be bound by any health claims, it is believed that the reduction of normally occurring (commensal) oral bacteria in the normally occurring oral microbiota, for example, by aggressive dental hygiene practices, may serve to make non-pathogenic antigens, such as pollen, more prevalent and visible to the immune system. It is further believed, that as a result, non-pathogenic antigens, such as those related to allergens as well as oral and/or sinus infections may be more readily targeted by the immune system, leading to exacerbated allergic reactions.

For example, oral hygiene hypothesis (OHH) is one aspect of a more general hygiene hypothesis (HH), which was proposed more than two decades ago (see Strachan, D. P. "Hay fever, hygiene, and household size", British Medical Journal 299, 1259-1260 (1989)) to explain the rise in allergic diseases. Numerous scientific studies have since provided support for HH, generally showing a relation between increased exhibition of allergies in association with modern social practices, such as formula infant feeding, antibiotic use, urban living, and reduction in family size (see e.g., Okada, H., Kuhn, C., Feillet, H. & Bach, J. F., "The hygiene hypothesis for autoimmune and allergic diseases: an update" Clin. Exp. Immunol. 160, 1-9 (2010)). Although the molecular mechanisms of immune system modulation by gut microbiota are well understood, efforts to reduce allergic reactions through microbial intervention, such as by the use of probiotics have shown inconsistent results.

Extensive oral hygiene practices, according to oral hygiene hypothesis (Han, C S., "A specific hygiene hypothesis" Med. Hypotheses 2016 August; 93:146-149), are believed to cause the exacerbation of naturally occurring respiratory allergies, such as allergic rhinitis (AR), one of the most common allergic conditions.

There is therefore a need for a composition including an oral cavity microbiota promoting substance and method of using the same that has the effect of promoting a healthy oral microbiota that promotes the healthy operation of the immune system which may have the functional effect of promoting an improved response to allergens as well as oral and/or sinus commensal bacteria, which may be the cause of oral and/or sinus infections.

It is an object of the invention to provide a composition including an oral cavity microbiota promoting substance and method of using the same that has the effect of promoting a healthy oral microbiota that promotes the healthy operation of the immune system which may have the functional effect of promoting an improved response to allergens as well as other oral and/or sinus commensal bacteria, which may be the cause of oral and/or sinus infections.

SUMMARY

A method of promoting a desired oral microbiota to treat an oral and/or sinus infection condition in a subject in need of such treatment including providing a preformulated prebiotic edible composition including an amino acid containing ingredient comprising individual molecules of L-arginine; substantially removing a biofilm from surfaces within an oral cavity by heating the inside of the oral cavity to a temperature of about 100 deg F. to about 130 deg F.; wherein following removal of the biofilm, the composition is provided contained and at least partially dissolved within an oral cavity of the subject for a period of at least from about 30 seconds to about an hour on a daily basis of at least two consecutive days to promote an increased concentration of selected oral microbiota, the selected microbiota comprising *Veillonella* and *Streptococcus*, thereby treating the oral and/or sinus infection condition.

DETAILED DESCRIPTION

The following detailed description is merely exemplary in nature and is not intended to limit the described embodiments or the application and uses of the described embodiments. As used herein, the word "exemplary" or "illustrative" means "serving as an example, instance, or illustration." Any implementation described herein as "exemplary" or "illustrative" is not necessarily to be construed as preferred or advantageous over other implementations. All of the implementations described below are exemplary implementations provided to enable persons skilled in the art to practice the disclosure and are not intended to limit the scope of the appended claims. Furthermore, there is no intention to be bound by any expressed or implied theory presented in the preceding technical field, background, brief summary or the following detailed description.

It is believed, and has been found that according to the oral hygiene hypothesis (OHH) noted above, that persistent and intensive hygiene practices, together with other life events, such as fever and/or antibiotic usage, will likely change the oral microbiota of an individual. The oral cavity is a complex environment with many different biological niches, such as the tongue, gum, and teeth. Normally occurring microbiota associated with these niches are different and are believed to have a different effect on normal functioning of the immune system.

Likewise, it is believed, and has been unexpectedly found, that the introduction of selected microbiota-promoting substances into the oral cavity in a controlled manner, may promote desired naturally occurring oral bacteria species/strains, which may in turn have an associated effect of modulating or reducing the intensity of certain types of oral and/or sinus infections and/or allergic reactions, including those associated with allergic rhinitis (AR) one of the most common allergic reactions including symptoms such as any combination of a runny or stuffy nose, sneezing, itchy/red eyes, coughing, and congestion.

While not intending to be bound by any particular theory of operation, and making no specific health claims, it is believed that oral microbiota interact with the host largely through metabolites produced by its relevant bacterial members. Those metabolites, such as but not limited to short chain fatty acid, may influence the function of multiple biologic systems and organs, such as the immune system. Missing or severe reduction of the relevant naturally occurring beneficial (commensal) bacteria may cause malfunctioning of the immune system, such as causing over sensitivity to commensal bacteria and/or allergens. Commensal microflora (normal microflora, indigenous microbiota) consists of those micro-organisms, which are present on body surfaces covered by epithelial cells and are exposed to the external environment (gastrointestinal and respiratory tract, vagina, skin, etc.).

Under specific conditions, the commensal bacteria may become opportunistic pathogens and may overcome protective host responses and exert pathologic effects. Therefore, in one embodiment it is believed that the immune system response to the allergens and/or commensal bacteria may be modulated by the method and/or composition such that the associated oral and/or sinus infections and/or allergic reaction symptoms are suppressed relative to what an infection and/or allergic reaction may be with an unhealthy level of, or different commensal microbiota. It is further believed and evidence suggests that over time, as a result of promoting a healthy oral microbiota with selected microbiota-promoting substances that the immune system may function in a healthy manner with a health promoting response to allergens and/or commensal bacteria that have become pathogenic.

Furthermore, due to the connectivity among mouth and respiratory duct and lungs, a healthy oral microbiota may lead to a healthy microbiota in the lungs as well. Eventually the method and/or composition may benefit the healthy functioning of the immune system which may in turn have a healthy response not only to oral and/or sinus infections and/or allergic rhinitis but also the relevant diseases in the lungs, such as asthma.

For example, in other embodiments, the method and/or composition may benefit the healthy functioning of a sensitized immune system with respect to oral and/or sinus infections including airway related infections including but not limited to gingivitis, periodontitis (periodontal disease), tonsillitis, rhinosinusitis, pharyngitis, and laryngitis. While some or a portion of these infections may be caused by pathogen invasion, a sensitized immune system attacking commensal bacteria may lead to the exacerbation and/or cause of infections associated with other opportunistic (pathenogenic) commensal bacteria caused infections.

The method and/or composition may be used to promote a healthy functioning of an immune system e.g., by reducing immune system sensitivity by restoring a healthy level of desired commensal bacteria to thereby at least reduce or alleviate symptoms associated with the infections and/or allergens.

In one embodiment, an oral microbiota promoting composition may be provided into an oral cavity that may have the effect of promoting desired microbiota within an oral cavity.

In another embodiment, a method of applying an oral microbiota promoting composition (prebiotic) may be provided that may have the effect of promoting desired microbiota within an oral cavity and have the desired functional effect of treating oral and/or sinus infections including airway infections and/or allergic reaction respiratory conditions including allergic rhinitis.

In one embodiment, a method of applying an oral microbiota promoting composition may include multiple instances of introduction of the composition into the oral cavity (mouth) in the form or a solid, powder, paste, or liquid in the amount of about 1 gm to about 500 gms at one time or multiple times in fractional amounts. Where the oral microbiota promoting composition is in the form of liquid, the method may include dissolving the composition in a liquid In another embodiment, a method of applying an oral microbiota promoting composition may include swallowing the composition following introduction of the composition into the oral cavity and following a period of retaining the composition within the mouth for a select period of time including e.g., chewing, gargling, and/or sublimating (dissolving) the composition while within the oral cavity.

In another embodiment, a method of applying an oral microbiota promoting composition may include removing the composition following introduction into the oral cavity by expelling (e.g., pulling out or spitting-out) the microbiota promoting composition following a period of retaining the composition within the mouth.

In another embodiment, a method of applying an oral microbiota promoting composition may include retaining the microbiota promoting composition within the oral cavity from about 10 seconds to about an hour, more preferably, from about 5 minutes to about 30 minutes on a daily basis for a period of about 2 days to about 60 days.

In another embodiment, a method of applying an oral microbiota promoting composition may include introducing the microbiota promoting composition for relatively short periods several times a day, for example from about 1 second to about 30 seconds, each from about 3 to about 10 times a day for a period of about 2 days to about 60 days.

In another embodiment, a method of applying an oral microbiota promoting composition may include extending the periods of introduction of the microbiota promoting composition into the oral cavity, for example, from about every 3 days to about every 10 days, including stopping the introduction of the composition following the disappearance of allergy symptoms.

In another embodiment, a method of applying an oral microbiota promoting composition may include at least partially removing a mucosal film (biofilm) from within the oral cavity prior to or while administering the microbiota promoting composition to the oral cavity.

It will be appreciated that the biofilm may be at least partially removed, including substantially removed (e.g., greater than about 95%), by raising the whole body temperature for a short time, for example, with conventional biological or physical means.

In a related embodiment, the biofilm may be at least partially removed by rinsing out (optionally including scrubbing or rubbing) the oral cavity (mouth) with a heated water containing liquid, such as water, at a temperature of from about to about 130 degrees Fahrenheit prior to applying the oral microbiota promoting composition to the oral cavity. It will be appreciated that rinsing with a hot water containing fluid as noted may advantageously at least partially remove a biofilm from surfaces within the oral cavity, thereby improving the operation of the oral microbiota promoting composition. The oral rinsing may include periodic rinsing, for example, each for about 10 seconds to about 30 seconds over a period of from about 5 to about 15 minutes.

In another embodiment, a method of applying an oral microbiota promoting composition may include at least one of brushing and rubbing portions of the oral cavity with the hot water containing fluid at a temperature of from about 100 to about 130 degrees Fahrenheit including at least the tongue, for example, with at least one of a brush, such as a toothbrush, and/or a wet cloth.

In another embodiment, the oral microbiota promoting composition may be formulated into oral dosage forms such as tablets, caplets, and capsules, or a powder formulation or that may be dissolved in a liquid, for example diluted in a liquid having a ratio of from about 1:1 to about 1:500 with respect to either weight or volume of the liquid (e.g., the liquid being larger number).

In another embodiment, the oral microbiota promoting composition may be formulated or manufactured as a chewing gum or candy, or other edible carrier, for example as an additive having a ratio of from about 1:1 to about 1:500 with respect to either weight or volume of the edible carrier (e.g., larger number).

In another embodiment, the oral microbiota promoting composition may be formulated as an additive to an oral hygiene product acting as a carrier, such as toothpaste or mouthwash, the microbiota promoting composition having a ratio of from about 1:1 to about 1:500 with respect to either weight or volume of the oral hygiene product.

In another embodiment, the oral microbiota promoting composition may be provided on bioadhesive delivery devices such as bioadhesive strips that are known in the art. For example, the composition may be provided on or infused into a bioadhesive strip, such as on a bioadhesive or self-adhesive support which supports the composition. For example, the composition may be included in a gel, such as a carbohydrate based gel that may be supported on a solid support, such as a plastic or cross-linked polymer support that may include micro-patterns on a supporting surface (e.g., having spacings of about 0.1 to about 2 mm). The bioadhesive strip infused with or supporting the oral microbiota promoting composition may be self-adhesive (in the presence of oral saliva) to dental or mucosal portions of the oral cavity.

In another embodiment, in a method of manufacturing an oral microbiota promoting composition may be formulated having an edible foodstuff as a carrier, the microbiota promoting composition having a ratio of from about 1:1 to about 1:500 with respect to either weight or volume of the edible foodstuff.

In one embodiment, the desired microbial species/strains promoted in the oral cavity by the oral microbiota promoting composition may be naturally occurring within the oral cavity and/or may be provided separately or within the oral microbiota promoting composition.

In a related embodiment, the desired microbial species/strains may be present in the oral cavity or in the oral microbiota promoting composition at a level of from about 1000 to about 1,000,000,000 living cells.

It will be appreciated that the desired microbial species/strains may be naturally occurring and/or may be obtained commercially and handled in accordance with any applicable safety requirements.

In another embodiment, the desired microbial species/strains promoted in the oral cavity by the oral microbiota promoting composition may include at least a first microbial species that can attach to surfaces (e.g., teeth, tongue, mouth) within the oral cavity and at least one second microbial species that may attach to the same or different surfaces and/or may attach to the at least first microbial species.

In a related embodiment, the at least a first and second microbial species may produce a product, such as a sugar containing moiety, that may be metabolized by the other of the at least a first and second microbial species.

In one embodiment, one of the desired microbial members promoted within the oral cavity promoted by the oral microbiota promoting composition may include one or more live bacterium with lactate fermenting capability such as, but not limited to *Veillonella*, which further may include one or more of associated species, such as, but not limited to, *Veillonella (V.) Dispar* and *Veillonella (V.) Parvula*.

In one embodiment, one of the desired microbial species/strains promoted within the oral cavity promoted by the oral microbiota promoting composition may include one or more live lactic acid producing bacterium such as but not limited to *Streptococcus* including one or more of associated species, such as, but not limited to, *Streptococcus (S.) salivarius* and *Streptococcus (S.) thermophilus*.

In a related embodiment, the desired microbial species/strains promoted within the oral cavity by the oral microbiota promoting composition may include at least one live lactic acid producing bacterium and at least one live lactate fermenting bacterium such as, but not limited to, respectively, *Veillonella* and *Streptococcus* and their respectively associated preferred species stated above.

In another embodiment, an oral microbiota promoting composition is provided that includes at least one amino acid or amino acid containing substance including at least L-arginine. The at least one amino acid may further or alternately include at least one of L-cysteine, DL-aspartic acid, L-glutamic acid, L-serine and L-tyrosine including phosphates, salts, acids, and enzymes comprising the same.

In preferred embodiments, the at least one amino acid may be introduced into the composition including substantially (e.g., greater than about 90%) individual molecules (as opposed to amino acid chains) of a respective amino acid, or at least individual molecules of the amino acid L-arginine. In another embodiment, the at least one amino acid may be substantially decomposed into individual molecules of the amino acid following introduction into the oral cavity.

For example, it is believed, and has been observed that L-arginine residues in long or short peptide chains and may not accomplish the promotion of the desired microbiota within the oral cavity, including with the desired health promoting effect, including the promotion of *Veillonella* and *Streptococcus*.

In a related embodiment, the at least one amino acid, may be present in the oral microbiota promoting composition at a weight percent level of from about 0.1 wt. % to about 99.9 wt. %, more preferably, from about 5 wt % to about 95 wt %, even more preferably from about 20 wt % to about 80 wt %.

In another embodiment, an oral microbiota promoting composition is provided that includes at least one sugar containing substance and at least one amino acid containing substance. The at least one sugar containing substance may include at least one monosaccharide, disaccharide, oligosaccharide, and polysaccharide.

Exemplary monosaccharides may include but are not limited to aldohexoses such as but not limited to mannose including associated isomers, phosphates, salts, acids, and enzymes comprising the same.

Exemplary disaccharides may include but are not limited to disaccharides including at least one of galactose and glucose, such as but not limited to lactose, sucrose, malibiose, maltose, cellobiose and trehalose (also known as mycose or tremalose) including associated isomers, phosphates, salts, acids, and enzymes comprising the same.

Exemplary oligosaccharides may include but are not limited to trisaccharides including at least one or more of galactose, glucose, and fructose, such as but not limited to raffinose (also known as melitose), stachyose, and verbascose, including associated isomers, phosphates, salts, acids, and enzymes comprising the same.

Further, Exemplary polysaccharides may include but are not limited to one or more polysaccharide polymers, such as, but not limited to polysaccharides including malotriose units, including but not limited to pullulan, and fructose polymers, such as, but not limited to inulin and further including associated isomers, phosphates, salts, acids, and enzymes comprising the same.

In a related embodiment, the at least one disaccharide may be present in the oral microbiota promoting composition at a weight percent level of from about 0.1 wt. % to about 99.9 wt. %, more preferably, from about 5 wt % to about 95 wt %, even more preferably from about 20 wt % to 80 wt %.

In a related embodiment, the at least one oligosaccharide may be present in the oral microbiota promoting composition at a weight percent level of from about 0.1 wt. % to about 99.9 wt. %, more preferably, from about 5 wt % to about 95 wt %, even more preferably from about 20 wt % to 80 wt %.

In a related embodiment, the at least one polysaccharide may be present in the oral microbiota promoting composition at a weight percent level of from about 0.1 wt. % to about 99.9 wt. %, more preferably, from about 5 wt % to about 95 wt %, even more preferably from about 20 wt % to 80 wt %.

In another embodiment, the oral microbiota promoting composition may include at least one prebiotic fiber. Exemplary prebiotic fibers may include but are not limited to inulin.

In a related embodiment, the at least one prebiotic fiber may be present in the oral microbiota promoting composition at a weight percent level of from about 0.1 wt. % to about 99.9 wt. %, more preferably, from about 5 wt % to about 95 wt %, even more preferably from about 10 wt % to 30 wt %.

In another embodiment the oral microbiota promoting composition may include additives such as one or more of carbohydrates, amino acids, salts, flavorants, proteins, surfactants, emulsifiers, flavonoids, alcohols, synthetic sweeteners, food preserving agents, and combinations thereof.

In one embodiment, the oral microbiota promoting composition may further include conventional foodstuffs such as one or more of brown sugar, syrup, honey, chocolate, nuts, almonds, spices, cinnamon, and vanilla.

In another embodiment, the oral microbiota promoting composition may further include extract from fruits, such as jujube fruit extract which may include one or more of rhamnose, xylitol, arabitol, fructose, glucose, inositol, sucrose, and maltose.

In a specific exemplary embodiment, an example of making an edible Foodstuff oral microbiota promoting composition is provided below in Example 1:

Example 1

1 cup raffinose
1 cup trehalose
2 tablespoons mannose
1 cup lactose
½ cup maltose
½ cup L-arginine
2 tablespoons pullulan
1 cup inulin
1 cup dark brown sugar
½ cup corn syrup
½ cup honey
1 cup milk chocolate
1 cup chocolate chips
¼ cup toasted almonds (small chips)
¼ tablespoon cinnamon
¼ tablespoon vanilla extract In one embodiment, the above ingredients may be admixed and heated to a temperature sufficient to melt or liquefy, preferably avoiding boiling for an extended period and then poured into a container to cool.

In another embodiment, live bacterium, in accordance with safety requirements or limitations, may be added following cooling (e.g., as a coating). It will be appreciated that adding the bacterium may be limited by applicable safety precautions and may reduce the shelf life of the product.

Although the embodiments of this disclosure have been described with respect to certain exemplary embodiments, it is to be understood that the specific embodiments are for purposes of illustration and not limitation, as other variations will occur to those of skill in the art.

What is claimed is:

1. A method of promoting a desired oral microbiota to treat an oral and/or sinus infection condition in a subject in need of such treatment comprising:
providing a preformulated prebiotic edible composition comprising an amino acid containing ingredient comprising separate individual molecules of L-arginine;
substantially removing a biofilm from surfaces within an oral cavity comprising heating the inside of the oral cavity to a temperature of about 105 deg F. to about 130 deg F.;
wherein following removal of the biofilm, the composition is contained and at least partially dissolved within an oral cavity of the subject for a period of at least from about 30 seconds to about an hour on a daily basis of at least two consecutive days in an effective amount to selectively promote an increased concentration of selected oral microbiota, the selectively promoted microbiota comprising *Veillonella* and *Streptococcus*, thereby treating the oral and/or sinus infection condition.

2. The method of claim 1, wherein the oral and/or sinus infection condition comprises one or more of gingivitis, periodontitis, tonsillitis, rhinosinusitis, pharyngitis, and laryngitis.

3. The method of claim 1, wherein the composition is provided in a carrier.

4. The method of claim 3, wherein the carrier comprises a solid, powder or liquid.

5. The method of claim 3, wherein the carrier comprises one or more of a chewable tablet, an edible capsule, and a hygienic paste, and an edible food.

6. The method of claim 3, wherein the carrier is supported on a bioadhesive strip configured for adhesion within an oral cavity.

7. The method of claim 1, wherein the composition is provided within the oral cavity from a period of from about 2 consecutive days to about 60 consecutive days.

8. The method of claim 1, wherein heating the inside of the oral cavity comprises periodic oral rinsing with a heated liquid, each rinsing for about 10 seconds to about 1 minute over a period of from about 5 to about 15 minutes.

9. The method of claim 8, wherein removal of the biofilm comprises at least one of brushing and rubbing the oral cavity with the heated liquid.

10. The method of claim 1, wherein the at least one amino acid further comprises at least one of L-cysteine, DL-aspartic acid, L-glutamic acid, L-serine, and L-tyrosine.

11. The method of claim 1, wherein the amino acid containing ingredient is present in the composition at a weight percent level of from about 0.1 wt. % to about 99.9 wt. %.

12. The method of claim 1, wherein the amino acid containing ingredient is present in the composition at a weight percent level of from about 5.0 wt. % to about 95.0 wt.

13. The method of claim 1, wherein the composition further comprises a sugar containing ingredient, the sugar comprising one or more of monosaccharides, disaccharides, oligosaccharides, and polysaccharides.

14. The method of claim 13, wherein the sugar comprises one or more of mannose, lactose, malibiose, maltose, cellobiose, trehalose, raffinose, stachyose, and verbascose.

15. The method of claim 13, wherein the composition further comprises polysaccharide polymers.

16. The method of claim 15, wherein the polysaccharide polymers comprise one or more of pullulan and inulin.

17. The method of claim 13, wherein the sugar ingredient comprises jujube fruit extract comprising one or more of rhamnose, xylitol, arabitol, fructose, glucose, inositol, sucrose, and maltose.

18. The method of claim 13, wherein the sugar is present in the composition at a weight percent level of from about 0.1 wt. % to about 95 wt. %.

19. The method of claim 13, wherein the sugar is present in the composition at a weight percent level of from about 0.5 wt. % to about 95 wt. %.

20. The method of claim 13, wherein the sugar is present in the composition at a weight percent level of from about 5.0 wt. % to about 95.0 wt. %.

21. The method of claim 1, wherein at least one of the composition and oral cavity further comprises live bacteria comprising a lactic acid producing bacterium and a lactate fermenting bacterium at a level of from about 1000 to about 1,000,000,000 living cells.

22. The method of claim 1, wherein *Streptococcus* includes one or more of *S. salivarius* and *S. thermophilus* and wherein *Veillonella* comprises one or more of *V. Dispar* and *V. Parvula*.

23. A method of promoting a desired oral microbiota to treat an oral and/or sinus infection condition in a subject in need of such treatment comprising:
providing a preformulated prebiotic edible composition comprising an amino acid containing ingredient comprising separate individual molecules of L-arginine;
substantially removing a biofilm from surfaces within an oral cavity comprising heating the inside of the oral cavity to a temperature of about 100 deg F. to about 130 deg F. over a period of from about 5 to about 15 minutes;
wherein following removal of the biofilm, the composition is contained and at least partially dissolved within an oral cavity of the subject for a period of at least from about 30 seconds to about an hour on a daily basis of at least two consecutive days in an effective amount to selectively promote an increased concentration of selected oral microbiota, the selectively promoted microbiota comprising *Veillonella* and *Streptococcus*, thereby treating the oral and/or sinus infection condition.

* * * * *